US00PP28000P2

(12) United States Plant Patent
Hartman

(10) Patent No.: US PP28,000 P2
(45) Date of Patent: May 9, 2017

(54) ***CALADIUM* PLANT NAMED 'PSY LAV 2322-566B'**

(50) Latin Name: *Caladium×hortulanum*
Varietal Denomination: PSY LAV 2322-566B

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,537

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'PSY LAV 2322-566B', characterized by its compact, short in height, upright and uniformly mounded plant habit; vigorous growth habit and rapid growth rate; lance-type leaves that are mostly lavender pink in color with red purple-colored venation, dark green-colored margins and random pale whitish lavender pink-colored spots; and above average tolerance to *Xanthomonas* Leaf Spot.

4 Drawing Sheets

Botanical designation: *Caladium×hortulanum.*
Cultivar denomination: 'PSY LAV 2322-566B'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'PSY LAV 2322-566B'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium×hortulanum* 'Carolyn Whorton', not patented, as the female, or seed, parent with *Caladium×hortulanum* 'Gingerland', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PSY LAV 2322-566B'. These characteristics in combination distinguish 'PSY LAV 2322-566B' as a new and distinct *Caladium* plant:

1. Compact, short in height, upright and uniformly mounded plant habit.
2. Vigorous growth habit and rapid growth rate.
3. Lance-type leaves that are mostly lavender pink in color with red purple-colored venation, dark green-colored margins and random pale whitish lavender pink-colored spots.
4. Above average tolerance to *Xanthomonas* Leaf Spot.

Plants of the new *Caladium* differ primarily from plants of the female parent, 'Carolyn Whorton', in the following characteristics:

1. Plants of the new *Caladium* have lance type leaves whereas plants of 'Carolyn Whorton' have fancy type leaves.
2. Plants of the new *Caladium* and 'Carolyn Whorton' differ in leaf color as leaves of 'Carolyn Whorton' are olive green in color with pink-colored blotches and bright red to rose pink-colored venation.
3. Plants of the new *Caladium* and 'Carolyn Whorton' differ in leaf petiole color as leaf petioles of 'Carolyn Whorton' are tan pink in color with darker stippling.

Plants of the new *Caladium* differ primarily from plants of the male parent, 'Gingerland', in the following characteristics:

1. Plants of the new *Caladium* and 'Gingerland' differ in leaf color as leaves of 'Gingerland' have white-colored interveinal areas, white and pink-colored venation, dark red-colored spots and green-colored borders.
2. Plants of the new *Caladium* and 'Gingerland' differ in leaf petiole color as leaf petioles of 'Gingerland' are tan pink to tan green in color with dark green-colored stippling, streaks and tessellations.

Plants of the new *Caladium* can be compared to plants of *Caladium×hortulanum* 'Lance Whorton', not patented. In side-by-side comparisons, plants of the new *Caladium* differ primarily from plants of 'Lance Whorton' in the following characteristics:

1. Plants of the new *Caladium* and 'Lance Whorton' differ in leaf color as leaves of 'Lance Whorton' have dark green-colored interveinal areas, rose red-colored venation and pink-colored spots and blotches.
2. Plants of the new *Caladium* and 'Lance Whorton' differ in leaf petiole color as leaf petioles of 'Lance Whorton' are tan pink in color with darker streaks, stippling and tessellations.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differ primarily from plants of 'Florida Sweetheart' in the following characteristics:

1. Plants of the new *Caladium* and 'Florida Sweetheart' differ in leaf color as leaves of 'Florida Sweetheart' have dark pink-colored venation, rose pink-colored interveinal areas with greenish white-colored margins.
2. Plants of the new *Caladium* and 'Florida Sweetheart' differ in leaf petiole color as leaf petioles of 'Florida Sweetheart' are tan pink in color with darker stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'PSY LAV 2322-566B' in a container and grown in a shadehouse (tuber de-eyed).

The photograph at the top of the second sheet is a comparison view of typical potted plants of the female parent, 'Carolyn Whorton' (left), 'PSY LAV 2322-566B' (center) and the male parent, 'Gingerland' (right).

The photograph at the bottom of the second sheet is a comparison view of typical potted plants of 'Lance Whorton' (right), 'PSY LAV 2322-566B' (center) and 'Florida Sweetheart' (left).

The photograph at the top of the third sheet is a comparison view of typical plants of 'PSY LAV 2322-566B' grown in containers; the plant on the left has not had its tuber de-eyed and the plant on the right has had its tuber de-eyed prior to planting.

The photograph at the bottom of the third sheet is a side perspective view of typical plants of 'PSY LAV 2322-566B' grown in an open field.

The photograph at the top of the fourth sheet is a close-up view of typical freshly-harvested tubers and roots of 'PSY LAV 2322-566B'.

The photograph at the bottom of the fourth sheet is a close-up view of a typical inflorescence of 'PSY LAV 2322-566B'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old (vegetative plant photographs and description) and ten weeks old (inflorescence photograph and description), and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'PSY LAV 2322-566B'.

Parentage:

*Female, or seed, parent.*—*Caladium×hortulanum* 'Carolyn Whorton', not patented.

*Male, or pollen, parent.*—*Caladium×hortulanum* 'Gingerland', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description (outdoor nursery-grown plants).*—Appearance: Multi-segmented and somewhat flattened; individual segments ovate or irregular in shape. Height: About 2.6 cm. Diameter: About 2.9 cm to 5 cm. Segment height: About 1.8 cm. Segment diameter: About 2.3 cm. Axillary buds, height: About 5 mm. Texture: Thick, starchy; somewhat brittle. Color: Epidermis, freshly-harvested: Browner than 199D, 177D and 182D; outer skin, close to 199A and 200D. Epidermis, dried: Close to 200A. Cortical tissue: Close to 4D. Axillary buds: Close to 49D. Root description: Thick, fleshy contractile roots; color, close to 155C. Rooting habit: Sparse to medium density.

Plant description:

*Plant type.*—Herbaceous perennial; suitable as a potted plant in containers 15-cm to 25-cm and suitable as a landscape plant in shaded areas.

*Plant and growth habit.*—Compact, short in height, upright and uniformly mounded plant habit; vigorous and dense growth habit; rapid growth rate; potted plants in finished or saleable form in about eight weeks after planting tubers; leaf petioles and leaves arise from one or more growing points on tubers; petioles mostly upright and outwardly leaning with development.

*Plant height, from soil level to top of foliar plane, shadehouse-grown potted plants.*—About 25 cm to 32 cm.

*Plant height, from soil level to top of inflorescences, shadehouse-grown potted plants*.—About 20.5 cm.

*Plant diameter or spread, shadehouse-grown potted plants*.—About 48 cm to 55 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 4.2 cm to 5.4 cm. Width: About 1.2 cm to 1.4 cm. Shape: Wedge-shaped. Apex: Acute to acuminate. Base: Sheathing the stem. Color, inner surface: Close to N155C; colors and patterns on the outer surface are visible on the inner surface. Color, outer surface: Close to 196D and close to 147A tinged with close to 49D; streaked, stippled and tessellated with close to 147A tinged with close to 200C; with development, color becoming closer to 199B stained with close to 187A to 187B.

Leaf description:

*Arrangement and type*.—Alternate; simple; lance-type.

*Length, shadehouse-grown potted plants*.—About 16.5 cm to 19.5 cm.

*Width, shadehouse-grown potted plants, flattened*.—About 9 cm to 15.5 cm.

*Shape*.—Ovate to lanceolate.

*Apex*.—Acute.

*Base*.—Sagittate to peltate.

*Margin*.—Entire; wavy with broad undulations.

*Texture, upper and lower surfaces*.—Smooth, glabrous; somewhat rigid.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Midvein: Close to N187B and 185C tinged with close to 147B. Primary veins: Close to N187B tinged with close to 147B. Areas surrounding venation: Close to 186C and 185B to 185C. Interveinal areas: Close to 147A, 147B, 195B and 185C to 185D; variable spots, close to 185C and 155C. Margins: Towards the margins, close to 147A; thin margin, close to 187A. Basal notch: Close to 187B. Developing leaves, lower surface: Midvein: Close to 147C tinged with close to 182D. Primary veins: Close to 191A. Areas surrounding venation: Close to 185C and 185C to 185D. Interveinal areas: Close to 191A, close to 195C and close to 195C tinged with close to 186D. Margins: Thin margin, close to 187A. Basal notch: Close to 187C to 187D. Fully expanded leaves, upper surface: Midvein and primary veins: Close to 187C tinged with close to 59A. Interveinal areas: Close to 185C and close to 185D tinged with close to 186C; variable spots, close to 155C, between 147B and 146B, 185C to 185D and 186C. Margins: Towards the margins, close to 147A; thin margin, close to 187A. Basal notch: Close to 187A to 187B. Fully expanded leaves, lower surface: Midvein and primary veins: Close to 160D tinged and flecked with close to 185D and 182C to 182D. Interveinal areas: Close to 185D tinged with close to 186D; variable spots and sectors, close to 155A tinged with close to 186D; close to 185D tinged with close to 186D and close to 155A and 147B to 147C tinged with close to 146C. Margins: Towards the margins, close to 191A tinged with close to 189A; thin margin, close to 187A. Basal notch: Close to 187C.

*Petioles*.—Aspect: Initially upright and straight; with development, leaning outwardly; flexible. Length, shadehouse-grown potted plants: About 18 cm to 24 cm. Diameter, distally, shadehouse-grown potted plants: About 3 mm to 4.5 mm. Diameter, proximally, shadehouse-grown potted plants: About 5.5 mm to 9 mm. Texture: Smooth, glabrous; glaucous. Color, shadehouse-grown potted plants: Close to 147B tinged with close to 189A or faintly tinged with close to 186D with stippling, streaks, stripes and tessellations close to 200B tinged with close to 147A; below the leaf and petiole junction, close to 156D and close to 199D faintly tinged with close to 51 D. Wing length, shadehouse-grown potted plants: About 3.5 cm to 5.5 cm. Wing diameter, shadehouse-grown potted plants: About 7 mm. Texture, inner and outer surfaces: Smooth, glabrous. Luster, inner and outer surfaces: Slightly glossy. Wing color, shadehouse-grown potted plants: Inner surface: Close to N155C; colors and patterns on the outer surface are visible on the inner surface. Outer surface: Close to 196D tinged with close to 49D and 147C to 147D; stippling, streaks and tessellations close to 147A tinged with close to 200C.

Inflorescence description: Inflorescences observed on ten week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring and early summer in central Florida; flowers develop about ten weeks after growth commences; inflorescences last about three days before fading; inflorescences persistent.

*Spathe*.—Length, overall: About 6.6 cm. Length, distal open portion: About 3.8 cm. Length, proximal closed portion: About 2.8 cm. Width, distal open portion: About 3.8 cm. Depth, distal open portion: About 1.5 cm. Width, at constriction: About 1 cm. Width, proximal closed portion: About 2 cm. Shape: Obovate. Apex: Acute; hooked forward. Base: Obtuse. Margin: Entire. Texture, front and rear surfaces: Smooth, glabrous. Luster, front surface: Dull sheen. Luster, rear surface: Glaucous, dull sheen. Color, front surface: Distal open portion: Close to 155D variably tinged with close to 186C to 186D and 186B; with development, color becoming closer to 199B. Proximal closed portion: Close to 148D; towards the base, flushed, stippled and mottled with close to N186C and 187A; color does not change with development. Color, rear surface: Distal open portion: Close to 155C; center, marbled and streaked with close to 145B and 145C; color does not change with development. Proximal closed portion: Close to 147B, 147C and 138A to 138B; areas, close to 147C to 147D; color does not change with development.

*Spadix*.—Length, overall: About 6.6 cm. Length, male flower zone: About 3.3 cm. Length, sterile zone: About 1.5 cm. Length, female flower zone: About 1.8 cm. Diameter, male flower zone: About 8 mm. Diameter, sterile flower zone: About 5 mm. Diameter, female flower zone: About 7 mm. Shape: Columnar. Apex: Bluntly rounded, obtuse. Base: Obtuse. Aspect: Upright. Color, mature, male zone: Close to 10D. Color, mature, sterile zone: Close to 155B. Color, mature, female zone: Close to 155A and 159D. Male flowers: Quantity per spadix: About 120. Shape: Obovate. Height: About 2 mm. Diameter: About 3 mm. Pollen amount: Sparse. Pollen color: Close to 4D. Female flowers: Quantity per spadix: About 120. Shape: Obovate. Height: About 2 mm. Diameter: About 1 mm to 1.2 mm. Stigma color: Close to 155A. Ovary color: Close to 159D.

*Scape*.—Length: About 13.9 cm. Diameter: About 4.5 mm. Strength: Sturdy; flexible. Aspect: Mostly erect. Texture: Smooth, glabrous. Luster: Dull to slightly glossy; glaucous. Color: Close to 147A to 147B and tinged, streaked and stippled with close to 200B; just below spathe, close to between 147C and 146C and faintly tinged, streaked and stippled with close to 200B to 200C.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot and to have above average susceptibility to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'PSY LAV 2322-566B' as illustrated and described.

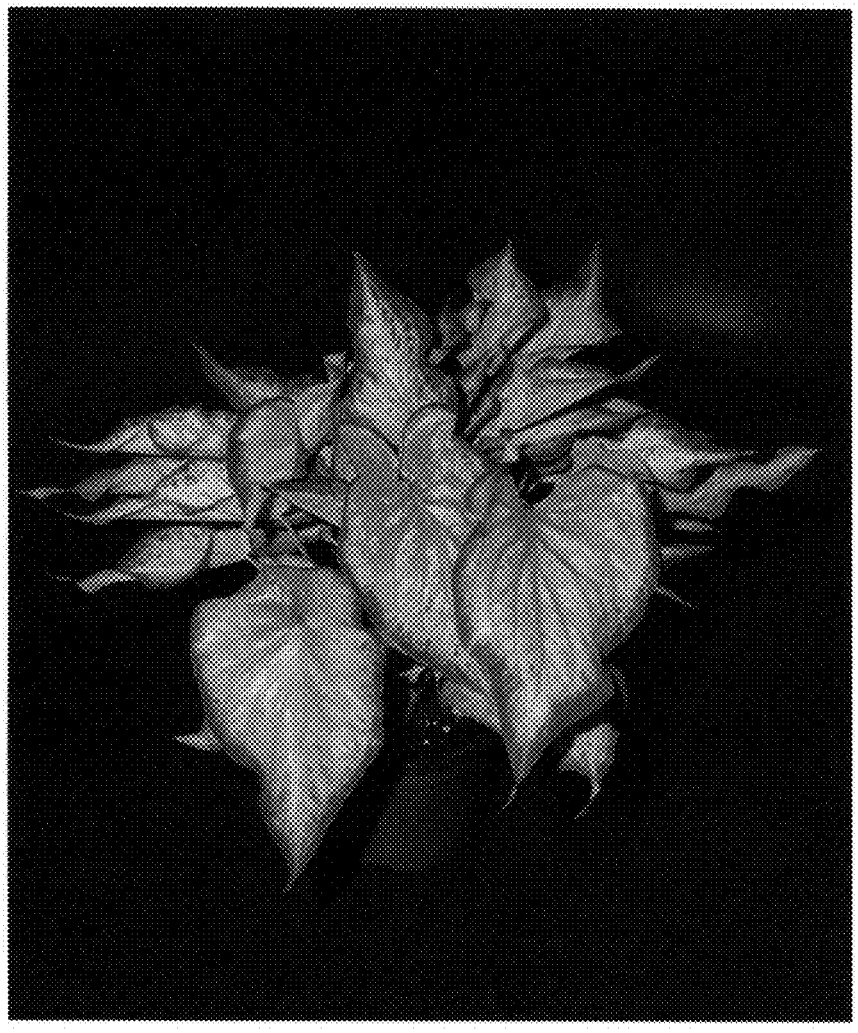

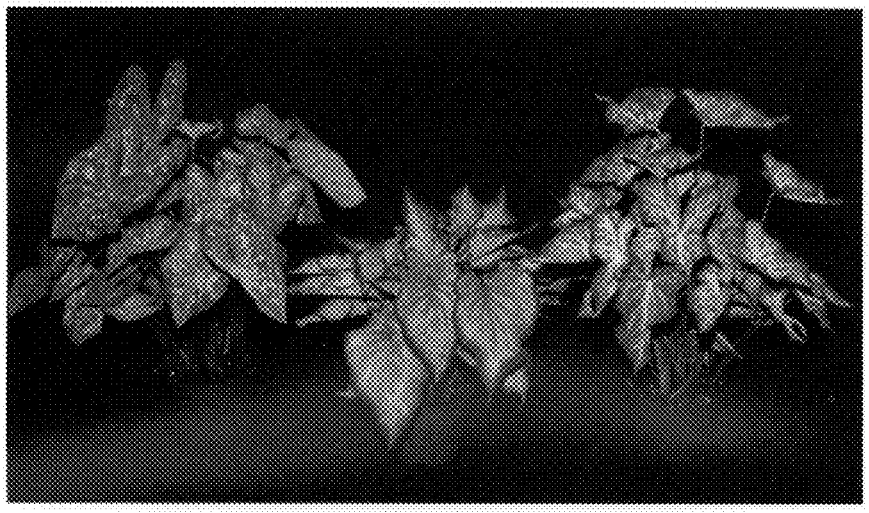
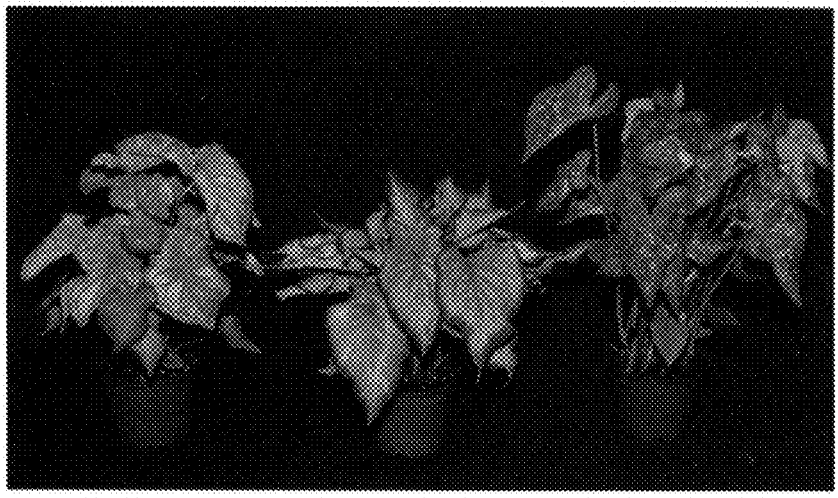

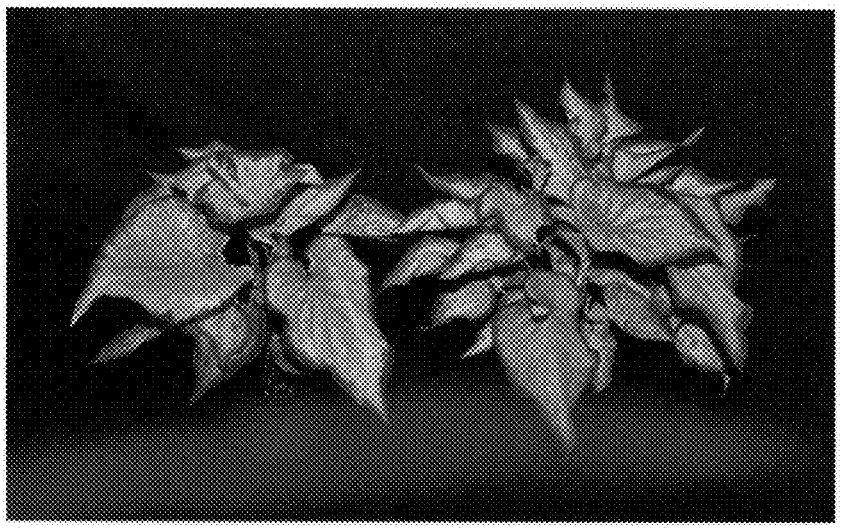
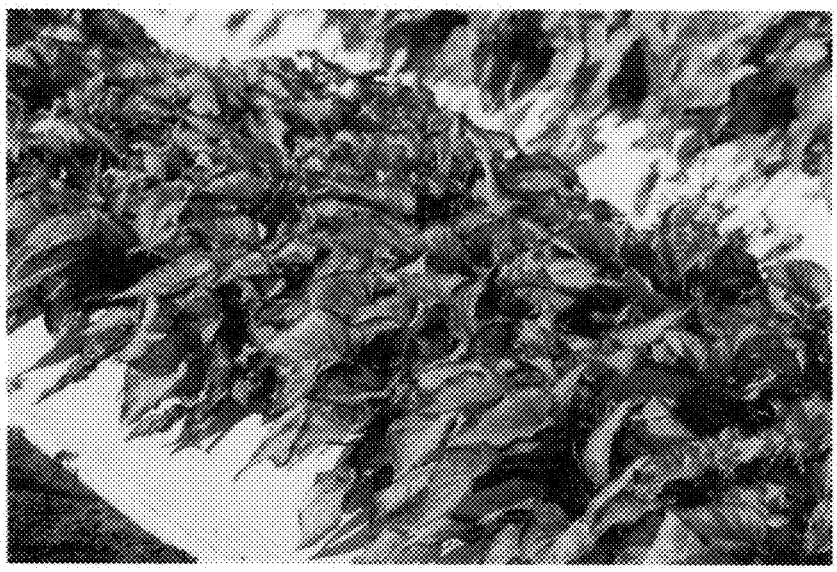

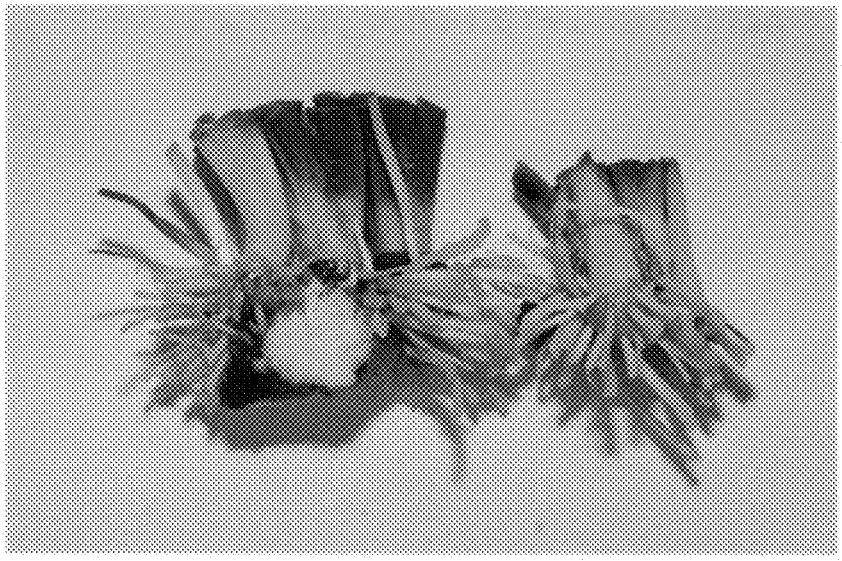
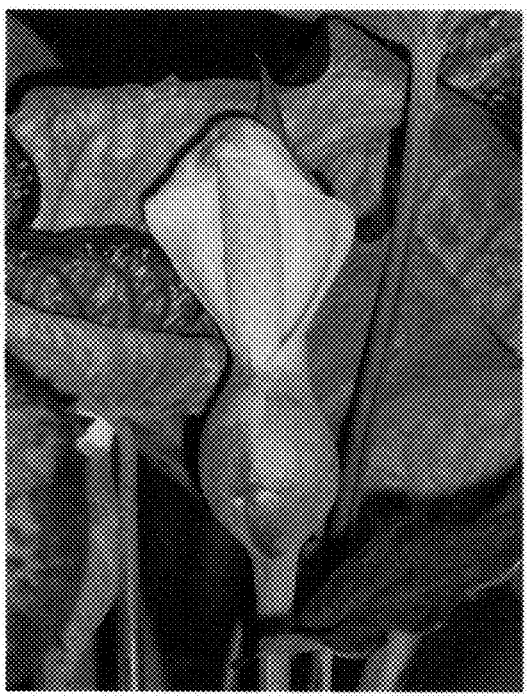

* * * * *